US012345690B2

(12) United States Patent
Berndt et al.

(10) Patent No.: US 12,345,690 B2
(45) Date of Patent: Jul. 1, 2025

(54) PROCESS AND SYSTEM FOR MONITORING AT LEAST ONE CONCENTRATION OF A GAS IN A MONITORED AREA

(71) Applicant: Dräger Safety AG & Co. KGaA, Lübeck (DE)

(72) Inventors: Malte Berndt, Lübeck (DE); Christof Rodehorst, Lübeck (DE); Raphael Maas, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 219 days.

(21) Appl. No.: 17/681,037

(22) Filed: Feb. 25, 2022

(65) Prior Publication Data

US 2022/0326202 A1     Oct. 13, 2022

(30) Foreign Application Priority Data

Mar. 2, 2021   (DE) ...................... 10 2021 105 011.1

(51) Int. Cl.
*G01N 1/26*   (2006.01)
*G01N 33/00*   (2006.01)
*G01N 1/02*   (2006.01)

(52) U.S. Cl.
CPC .......... *G01N 33/0008* (2013.01); *G01N 1/26* (2013.01); *G01N 33/0027* (2013.01);
(Continued)

(58) Field of Classification Search
CPC .. G01N 33/0008; G01N 1/26; G01N 33/0027; G01N 33/0065; G01N 33/0073; G01N 2001/021; G01N 33/0063; G01N 33/0075; H04W 4/50; H04W 4/021; H04L 67/12; H04L 67/125; G08B 21/12
See application file for complete search history.

(56) References Cited

U.S. PATENT DOCUMENTS

2011/0163892 A1   7/2011   Groves et al.
2014/0001779 A1 *  1/2014   Bedoian .................. E05B 47/00
                                                        292/336.3
(Continued)

FOREIGN PATENT DOCUMENTS

DE   102014015910 A1 *  5/2016  ......... G01N 33/0009
DE   202018100186 U1 *  3/2018  ............. G01D 11/24
(Continued)

*Primary Examiner* — Kristina M Deherrera
*Assistant Examiner* — Fatemeh Esfandiari Nia
(74) *Attorney, Agent, or Firm* — McGlew and Tuttle, P.C.

(57) ABSTRACT

A process and a system for monitoring at least one concentration of a gas in a monitored area includes generating data by a mobile gas measuring device (3a), whose position in the monitored area is determined or is known and transmitting the data directly or indirectly to a central data processing unit (1). The data are compared with at least one limit value, and an information signal is outputted by the at least one mobile gas measuring device and/or by the central data processing unit in case of an undershooting or overshooting of the limit value. The monitored area is divided into at least two zones (8) and zone-specific parameters are assigned to the zones. A functionality of the mobile gas measuring device is set and/or changed based on the current position of the gas measuring device and based on at least one of the zone-specific parameters.

18 Claims, 3 Drawing Sheets

(52) U.S. Cl.
CPC ..... *G01N 33/0065* (2013.01); *G01N 33/0073* (2013.01); *G01N 2001/021* (2013.01)

(56) References Cited

U.S. PATENT DOCUMENTS

| | | | |
|---|---|---|---|
| 2014/0031082 A1* | 1/2014 | Zishaan | G08B 21/14 |
| | | | 455/556.1 |
| 2015/0102926 A1 | 4/2015 | Kamalakannan et al. | |
| 2016/0334378 A1 | 11/2016 | Maddila et al. | |
| 2017/0047969 A1* | 2/2017 | Mroszczak | H04B 5/77 |
| 2018/0212832 A1* | 7/2018 | Baird | G08B 25/10 |
| 2019/0086378 A1* | 3/2019 | Holdcroft | G01N 33/0009 |
| 2019/0311599 A1* | 10/2019 | Jensen | G08B 29/02 |
| 2020/0378940 A1* | 12/2020 | Pariseau | G01N 33/0075 |
| 2022/0163497 A1* | 5/2022 | Moore | G01N 33/0006 |

FOREIGN PATENT DOCUMENTS

| | | | |
|---|---|---|---|
| EP | 2339556 A1 | | 6/2011 |
| EP | 2905760 A2 | | 8/2015 |
| JP | 2010267244 A | * | 11/2010 |

* cited by examiner

PROCESS AND SYSTEM FOR MONITORING AT LEAST ONE CONCENTRATION OF A GAS IN A MONITORED AREA

CROSS REFERENCE TO RELATED APPLICATIONS

This application claims the benefit of priority under 35 U.S.C. § 119 of German Application 10 2021 105 011.1, filed Mar. 2, 2021, the entire contents of which are incorporated herein by reference.

TECHNICAL FIELD

The present invention pertains to a process as well as to a system for monitoring at least one concentration of a gas or gas mixture in a monitored area with a mobile gas measuring device. For monitoring gas concentrations in the monitored area, data are generated with at least one mobile gas measuring device and are transmitted to a central data processing unit. The data generated on the basis of the gas concentration measurement are compared with at least one limit (threshold) value and an information signal is outputted depending on the result of the comparison by the mobile gas measuring device or by the central data processing unit.

TECHNICAL BACKGROUND

Mobile gas measuring devices are used for the protection of people working in the work areas for monitoring production sites, such as chemical plants or steel mills, refineries or mines, at which toxic, potentially explosive, high-oxygen or low-oxygen gas atmospheres may develop. The mobile gas measuring devices have suitable sensors in order to detect the concentration of gases or gas mixtures, which are present in the respective work area or may occur at a hazardous concentration. Further, the mobile gas measuring devices have elements that notify the device user and/or generate an alarm for him in case of a limit value violation.

Even if it would be desirable, for example, for risk analyses or for investigating hazardous situations and accidents, an automated analysis of the data provided by the mobile gas measuring devices is carried out nowadays without taking location information into consideration. Location-specific information in relation to a monitored production site and to the plants and hazardous sites arranged in different areas cannot for this reason be fully utilized. It is problematic in this connection that a plurality of work areas, which impose different requirements on the needed or approved tools, measuring devices and the operating staff, are provided at the often comparatively large and branched-out production sites and, in particular, different safety requirements are to be taken into consideration. The different safety requirements applicable to the respective work areas are not, above all, often directly perceptible for people who enter the corresponding areas. This is especially true if, e.g., work to be carried out requires the focus of the workers or a disturbance develops in a plant or a hazardous situation develops.

Systems in which it is possible to divide a production site into work areas and evacuation areas and to carry out a position determination for people who are located at the production site on the basis of a portable gas measuring device are known from the state of the art in this connection.

A corresponding system is known, for example, from EP 2 905 760 A2. As soon as a specific event occurs in a defined work area, an optimal escape route is displayed to the device user. Further, people who have not reached the evacuation area within a defined time are informed separately and the possibility of passing on an alarm from one device user to another device user is described.

Furthermore, a system in which the respective hazard potential is stored in a central data bank for different work areas is described in US 2015/0102926 A1. Employees who are allowed based on their skills and authorizations to enter the respective work area or to carry out work there are selected and the provision of these employees with the necessary tools and measuring devices is specified on the basis of this information. Alarms or notifications can be triggered if approval criteria stored in the memory are not met on the basis of a monitoring.

Further, a system in which limit values stored in a mobile gas measuring device are adapted as needed as soon as this mobile gas measuring device is moved from a specified work area into the next one is known from US 2016/334378 A. The basic properties and settings of a mobile gas measuring device do, however, remain unchanged according to the technical solution described.

SUMMARY

Based on the technical solutions known from the state of the art as well as on the above-described problems, a basic object of the present invention is to perfect a system as well as a process for monitoring a monitored area in respect to the gas concentration occurring there such that the mobile gas measuring devices used can be used in an especially flexible manner, without the personal safety of the device users being compromised thereby. It shall be possible during the use of a mobile gas measuring device to adapt the corresponding devices to the needs occurring in a work area and to adapt corresponding settings and work procedures of the measuring device in a suitable manner flexibly, rapidly and with high precision. It is of essential significance in this connection that a corresponding adaptation of a gas measuring device or the change of the settings is carried out such that the safety of the device user is not compromised hereby nor is the device user hindered in his activity.

The process and/or system to be proposed should thus be configured such that location-specific data present in a monitoring system can be used in an effective manner in order to achieve a highly accurate and reliable localization of a mobile gas measuring device with a needs-based adaptation, optimization and/or change of device parameters and/or settings. It should further be possible in this connection to bring about a change in the behavior of a mobile gas measuring device, which change goes beyond a change caused by the modification of individual device parameters.

The above-described object is accomplished with a process for monitoring at least one concentration of a gas or gas mixture in a monitored area according to the invention. Further, a system, with which the basic object of the present invention is accomplished, is described herein. Advantageous embodiments of the present invention are the subject of this disclosure and will be explained in more detail in the following description partially with reference to figures.

The present invention pertains to a process for monitoring at least one concentration of a gas or gas mixture in a monitoring step with the following steps:

generation of data by at least one mobile gas measuring device, which is located in the monitored area, on the basis of a gas concentration measurement and transmission of the data to a central data processing unit, comparison of the data generated on the basis of the gas concentration measurement with at least one limit (threshold) value and output of an information signal as a function of an undershooting or overshooting of the limit value by the at least one mobile gas measuring device and/or by the central data processing unit, as well as detection of a current position of the at least one mobile data processing unit.

The process according to the present invention is characterized by a division of the monitored area into at least two zones and by the setting of zone-specific parameters for the zones as well as by setting and/or changing at least one functionality of the at least one mobile gas measuring device on the basis of the current position of the gas measuring device and of at least one zone-specific parameter.

It is consequently significant for the process according to the present invention that, on the one hand, a location-specific identifier is assigned first to at least one mobile gas measuring device, which is located in the monitored area and which is moved at least from time to time, so that the mobile gas measuring device can unambiguously be located, and, on the other hand, that at least one functionality of the mobile gas measuring device, i.e., for example, a device-specific setting in reference to the measurements to be carried out, the type of the alarm generation for the device user, the manner of visualization of information and/or a limit value and/or threshold value stored in the device is changed as needed such that the location-specific information is taken into consideration. The functionalities of a mobile gas measuring device, i.e., settings that pertain to an operating mode and/or to the operating method, can thus be automated and, above all, adapted to the locally prevailing conditions and to the safety criteria to be complied with without the device user having to take any actions for this purpose. The area to be monitored is divided for this purpose into at least two zones, to which respective zone-specific parameters are assigned, which are stored in the central data processing unit and/or in at least one mobile gas measuring device. Taking into consideration the zone in which a respective mobile gas measuring device is located and the zone-specific parameters specified for this zone, the necessary functionalities are thus assigned to a mobile gas measuring device in a comparatively simple manner. The assignment is thus carried out always under the currently prevailing conditions and existing safety requirements.

It is conceivable in this connection to always update both the division of a production site into zones and the assignment of zone-specific parameters to the respective zones whenever this is necessary, for example, based on changes in the production process or because of newly erected or converted plants. Corresponding changes are preferably carried out in the central data processing unit and/or in the control of at least one mobile gas measuring device, so that no interventions are, as a rule, necessary in the hardware, e.g., in the sensor system, of the mobile gas measuring device being used. The at least one mobile gas measuring device (one or a plurality of mobile gas measuring devices can thus be adapted to the zone-specific parameters, especially to the conditions prevailing there, to necessary permits, to safety regulations to be taken into account and/or to the existing or possibly occurring hazards and be changed again when needed comparatively rapidly, with high accuracy and without changes having to be carried out for this purpose on hardware components of the devices themselves.

A sensitivity, an operating mode, a limit value stored in the mobile gas measuring device, a type of alarm generation, an alarm output loudness, a decision criterion for an automated forwarding of information, especially of alarms, and/or a setting of a display unit of the mobile gas measuring device, are set and/or changed on the basis of the current position and of at least one zone-specific parameter in a special embodiment of the process according to the present invention. Specific functionalities of a mobile gas measuring device are thus adapted as needed to the conditions and safety requirements prevailing in a zone of a production site according to this special embodiment. The individual zones of a production site can thus be distinguished, for example, in terms of the noise and light conditions prevailing there. It may likewise be necessary in a zone not to carry out certain actions of a gas measuring device because special conditions, e.g., loud production units, maintenance or repair areas and/or potentially explosive gas atmospheres are present here.

Furthermore, it is advantageous if the mobile gas measuring device outputs information as soon as it is moved from one zone into another zone. Corresponding information may be used, on the one hand, to call the device user's attention to the circumstance that he is moving now into another zone with possibly changed safety requirements and, on the other hand, to alert him to notify other people and/or the central data processing unit and thus, for example, the people working in a control room that the device user is now changing over from one zone to another, which may possibly lead to new requirements. It is further conceivable that it is checked automatically or by a guard staff in the control room during a change from one zone into another whether a device user has the qualification necessary for the specific zone and/or is carrying along the needed or approved tools and/or gas measuring device. If this is not the case, the device user is advantageously informed by a notification in the form of a text message or a verbal message or by a visually, acoustically or haptically perceptible alarm signal that he is not allowed to change over from one zone into another or is allowed to do so under certain conditions only. He can likewise be informed in this manner that he needs additional tools, measuring devices and/or assistants. As an alternative or in addition, it is conceivable that such information is outputted via an additional device, which is used for transmitting data, e.g., a smartphone.

Furthermore, it is conceivable that a data transmission, especially a wireless data transmission, is started or ended between the mobile gas measuring device and the central data processing unit on the basis of the current position of the mobile gas measuring device and of at least one of the zone-specific parameters. It is thus conceivable, for example, that a wireless data transmission is carried out only in defined zones intended for this, while no data transmission takes place in other zones, e.g., based on the safety requirements prevailing there. The data generated during this time are preferably stored in an internal memory of the mobile gas measuring device. It is likewise conceivable that a data transmission, especially a wireless data transmission, is established if the determination of the position of the mobile gas measuring device shows that this mobile gas measuring device is located in a zone in which a wireless data transmission is possible and permissible.

According to a special variant of the present invention, a calibration and/or testing procedure is started or ended in the gas measuring device on the basis of the current position of the mobile gas measuring device and of at least one of the zone-specific parameters. It is conceivable in this connection that a calibration and/or testing of the mobile gas measuring device takes place when it is located, for example, in a zone to which no special safety requirements apply and no limit value violation can consequently be expected in respect to the concentration of a gas or gas mixture either.

The gas measuring device is preferably located in a zone in which the gas needed for a test and/or a gas mixture is present and in which, e.g., a display unit can display the test results. According to a special variant, it is a chamber, into which the gas measuring device is inserted at least from time to time and in which a known atmosphere, whose composition as well as the concentration of the individual gas constituents are measured and the measured values are compared with the communicated values. A calibration of the gas measuring device is preferably carried out on the basis of the comparison of the measured values and the known or communicated values carried out.

The times spent in safe zones and/or in maintenance or service areas can advantageously be used precisely for actions of the mobile gas measuring device which should not be carried out in other, safety-critical zones, for example, because they would lead to limited protection. It is conceivable in this connection that a firmware or software update is started or ended on the basis of the current position of the mobile gas measuring device and of at least one zone-specific parameter. It is likewise possible also to carry out a corresponding update of a gas measuring device during the use in zones that are considered to be safe zones. It is not absolutely necessary based on this technical configuration to install necessary updates outside of the operating time proper of the gas measuring device. In particular, the gas measuring devices do not need to be collected separately for carrying out an update and it is not necessary to monitor the performance of an update. It is rather recognized in an automated manner whether a mobile gas measuring device is located in a safe zone or even in a maintenance and/or service area or else in a safety-critical zone, in which, e.g., no updates shall be installed.

According to a special embodiment of the present invention, a stationary localization module, which transmits an identification signal specific of the zone in which the stationary localization module is arranged, is arranged in at least one zone of the monitored area. It is generally conceivable that the identification signal is received by the at least one mobile gas measuring device or by a gateway, via which the mobile gas measuring device transmits data to the central data processing unit, and that it adds information on the position of the mobile gas measuring device and/or on the zone in which the mobile gas measuring device is located to the data transmitted by the mobile gas measuring device directly or via the gateway to the central data processing unit on the basis of the received identification signal. It is conceivable in this connection that a data transmission from the at least one mobile gas measuring device to the central data processing unit takes place via a gateway arranged stationarily in the monitored area. Such a gateway adds information on the position of the mobile gas measuring device and/or on the zone in which the mobile gas measuring device is located to the data transmitted by the mobile gas measuring device. The gateway is advantageously fastened in the area of a stationary gas measuring device or to said gas measuring device and it establishes at least from time to time a unidirectional or bidirectional data transmission path to the central data processing unit. It is further conceivable that a gateway is integrated into a mobile transceiver unit, for example, a mobile phone, or into another mobile device. The data transmission from the mobile gas measuring device to the central data processing unit preferably takes place in this case indirectly, for example, via a mobile phone, which is carried along by the user of the gas measuring device together with the mobile gas measuring device and which is integrated into the gateway.

As an alternative or in addition, it is possible that the gas measuring device transmits data directly to a central data processing unit and/or to a central memory, and a device-specific identifier, especially a so-called ID, is added to the transmitted data. The device-specific identifier is advantageously linked by the gas measuring device and/or by another device with information on the location of the gas measuring device, so that the location of the data generation and/or data transmission is available for a data processing.

At least one stationary gas measuring device, which generates data on the basis of a gas concentration measurement and transmits them to the central data processing unit, is arranged in the monitored area in another embodiment of the process according to the present invention. The data generated by means of the gas concentration measurement are compared in the central data processing unit with, for example, a limit value and an information signal is outputted in case of an undershooting or overshooting of the limit value by the at least one stationary gas measuring device and/or by the data processing unit. It is conceivable in this connection that the information signal represents a control signal, which is transmitted to an another device and it leads to an action here. For example, such an information signal may be transmitted to an output unit, such as a display or a horn, in order thus to bring about an alarm generation by the output unit. It is essential in this special embodiment that the information signal is transmitted to an actuator element, which may, but does not have to, be connected to a stationary gas measuring device and/or to the central data processing unit or be integrated into same, so that the actuator element is activated in order to carry out an alarm generation or another suitable action.

It is, furthermore, possible that a stationary gas measuring device establishes, at least from time to time, a unidirectional or bidirectional data transmission path to a mobile gas measuring device located within range. Data are transmitted in this case between a stationary gas measuring device and a mobile gas measuring device and it is possible, for example, to transmit an information signal or a notification from the central data processing unit via the stationary gas measuring device to a mobile gas measuring device. It is, furthermore, possible based on the known position of a mobile gas measuring device for the stationary gas measuring device, which is located within the range of the respective mobile gas measuring device to be notified, to be selected specifically for a data transmission. A localization module, which transmits an identification signal specific of the zone in which the stationary gas measuring device is located, is preferably arranged at the stationary gas measuring device.

Since the location of a stationary gas measuring device is stored, in general, in the system, it is, furthermore, possible to use this data transmission, which is embodied, for example, by means of Bluetooth Low Energy, in order to determine the location of a mobile gas measuring device located in the vicinity as soon as a stationary gas measuring device receives or transmits data, wherein an identification specific of the mobile gas measuring device is added to the respective data transmitted by the mobile gas measuring device either by the stationary gas measuring device, and preferably by the mobile gas measuring device. It is advantageously possible now for a stationary gas measuring device to transmit an identifier, which contains location-specific information that can be received and processed by another device, especially by a mobile gas measuring device, or makes it possible at least to locate a mobile gas measuring device located in the area surrounding the stationary gas measuring device, especially by a central data processing unit.

According to a preferred variant, the zone-specific parameters are set by taking into consideration light and/or noise conditions prevailing in the assigned zone, an expectable or existing contamination of the air with dust and/or vapor, gases or gas mixtures that are potentially to be expected to be present in the zone, a hazard potential, accessibility, plants and plant parts present in the zone and/or the tools and/or measuring devices needed in the zone. As is shown by this list, which is given only as an example, a number of possibilities are thus available for defining the requirements prevailing in a zone by means of corresponding zone-specific parameters and for providing them for selecting the needed functionalities, which can be activated or deactivated in a mobile gas measuring device. The process according to the present invention makes it possible in this manner to adapt a mobile gas measuring device to the respective conditions and safety requirements prevailing in a zone in a flexible manner, without the device user having to perform any actions for this or being distracted in another manner. The personal safety of a device user can thus be increased, because the necessary functions are active at any time in the mobile gas measuring device being carried along.

The present invention also pertains to a system for monitoring a concentration of a gas or gas mixture in a monitored area with at least one mobile gas measuring device for providing gas concentration-specific data, with a data processing unit, between which and the at least one mobile gas measuring device a unidirectional or bidirectional connection can be established at least from time to time for the data transmission, and with a unit for setting a current position of the mobile gas measuring device. The monitoring system according to the present invention is characterized in that the mobile gas measuring device and/or the central data processing unit are set up to assign the current position of the gas measuring device, which is set by the unit for setting a current position, to a zone of the monitored area, which zone is demarcated in space, and in that a change or setting of a functionality and/or of a device parameter of the mobile gas measuring device can be initiated by a control unit of the mobile gas measuring device and/or by the central data processing unit by taking into consideration the zone in which the mobile gas measuring device is located. The system according to the present invention is advantageously configured such that it can carry out the process for monitoring at least one concentration of a gas or gas mixture in a monitored area according to at least one of the above-described embodiments.

At least one stationary gas measuring device, which is set up for a unidirectional or bidirectional data transmission with the central data processing unit and/or with the at least one mobile gas measuring device, is arranged in the monitored area in a special embodiment of the monitoring system according to the present invention.

According to another special embodiment of the system according to the present invention, at least one localization module and/or at least one gateway are arranged in the monitored area. The localization module is set up here such that it transmits an identification signal, which is specific of the zone in which the localization module is located. The gateway is configured such that data, which provides information on the position of the mobile gas measuring device and/or on the zone in which the mobile gas measuring device is located, can be transmitted to the central data processing unit. Data that are transmitted from a mobile gas measuring device can be complemented in this manner with information on the position of the mobile gas measuring device and/or on the zone in which the mobile gas measuring device is located, especially when the mobile gas measuring device does not complement itself the generated data with such location-specific information.

The present invention will be explained in more detail below without limitation of the general inventive idea on the basis of special exemplary embodiments with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
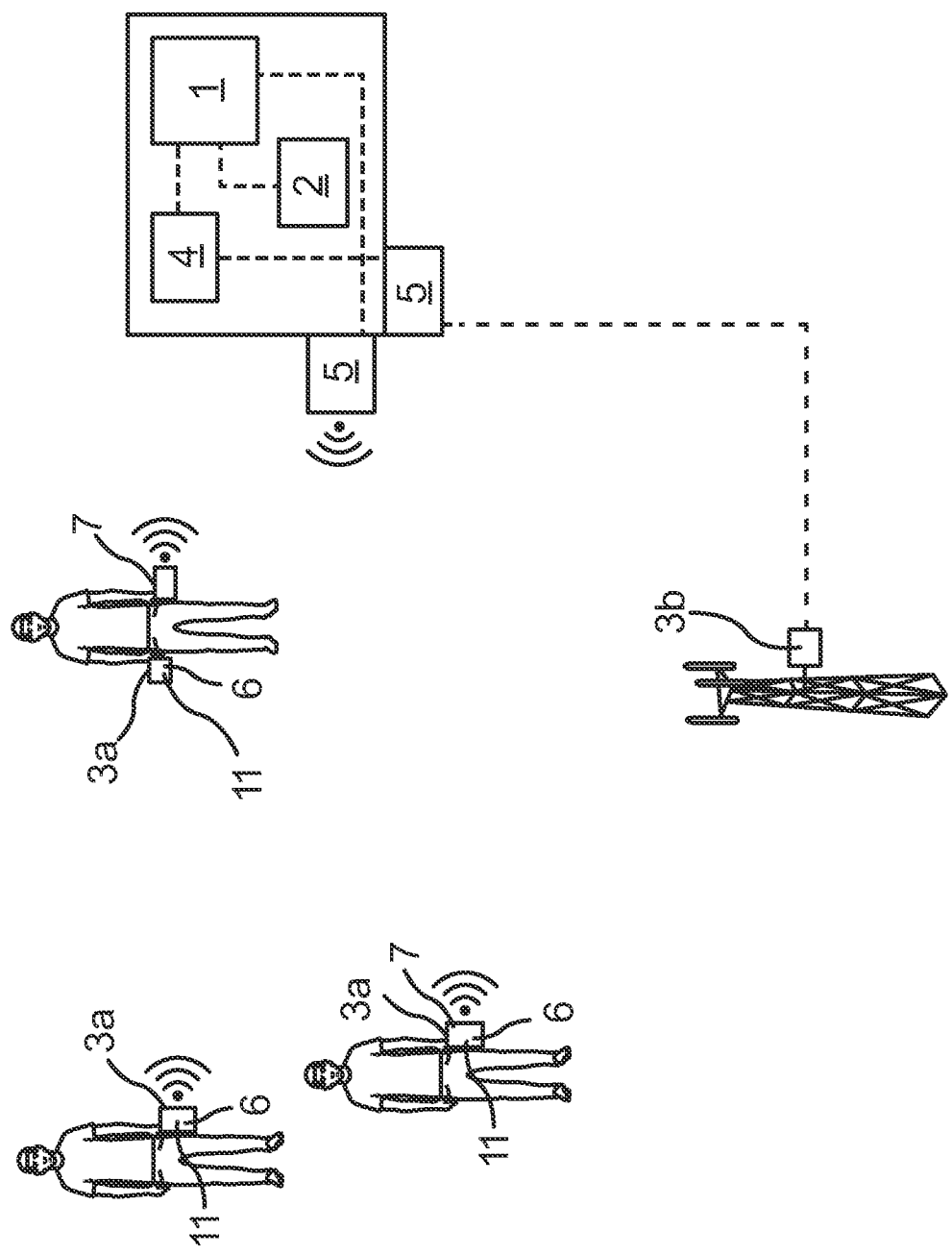
FIG. 1 is a schematic view of a system for monitoring the concentration of at least one gas or gas mixture in a monitored area of a production site.

Referring to the drawings, FIG. 1 schematically shows a system for monitoring the concentration of at least one gas or gas mixture in a monitored area of a production site, here a refinery, at which different chemical media are processed, conveyed, produced and/or transferred, especially in the liquid or gaseous form. The system shown schematically is suitable for monitoring the atmosphere in a plurality of work areas of the production site with respect to the presence of toxic gases or vapors, combustible or explosive atmospheres or an oxygen deficit. The monitoring system being shown has mobile and stationary gas measuring devices (3a, 3b), with which the concentration of individual gases or gas mixtures is detected and corresponding data can be transmitted to a central data processing unit 1 of a control room of the production site.

Both mobile and stationary gas measuring devices 3a, 3b are used as gas measuring devices for monitoring the production site shown schematically in FIG. 1. Mobile gas measuring devices 3a are used mainly for the protection of the people working in the work areas as well as for the clearance measurement of confined spaces and they have suitable sensors in order to detect the concentration of gases or gas mixtures, which are present in the respective work area or may occur in a hazardous concentration. Further, the mobile gas measuring devices 3a have, on the one hand, elements that inform the user of the device in the case of a limit (threshold) value violation or generate an alarm for him and, on the other hand, they have a unit, which makes possible, at least from time to time, the direct or indirect transmission of the generated data to a suitable interface 5 of the central data processing unit 1.

The stationary gas measuring devices 3b monitor above all special areas or plants in the monitored area of the production site for the presence of toxic, combustible, low-oxygen, high-oxygen or potentially explosive gases or gas mixtures in order for an alarm generation to be able to take place as rapidly as possible and for countermeasures, e.g., the avoidance of a hazardous situation, the avoidance of an incident or, if necessary, the putting of a plant out of operation, can be taken as rapidly as possible. The stationary gas measuring devices 3b have for this purpose a sensor or a plurality of sensors. The measured data generated continuously or intermittently are passed on for further processing to a suitable interface 5 of the central data processing unit 1 in the control room of the production site and they are processed there either immediately or after an intermediate storage in a central memory 4.

According to the embodiment shown in FIG. 1, the data generated in the different gas measuring devices 3a and 3b are transmitted to a suitable interface 5 of the central data processing unit 1 in a wireless or wired manner. The data are stored intermediately at least partially in a central memory 4 within the central data processing unit 1 and are analyzed by means of a data analysis unit 2.

It is essential for the system shown in FIG. 1 that the production site is divided into a plurality of zones 8 and zone-specific parameters are assigned to the individual zones 8 as a function of the conditions prevailing there and as a function of the necessary safety measures. As will be explained in more detail below, at least one functionality of the mobile gas measuring device 3a can be changed or adapted in a specific manner on the basis of a determination of the location at which a mobile gas measuring device 3a is located, of the assignment of the location to one of the zones 8 and of the zone-specific parameters set for the respective zone 8. A change is thus brought about in the system behavior in a suitable manner by means of the solution according to the present invention by taking into consideration the respective position of at least one mobile gas measuring device 3a, on the one hand, and different zone-specific parameters of the zones 8 of the production site, on the other hand, for the operation and/or for the selected operating mode of the mobile gas measuring device 3a. A location-dependent change in the functionality of a mobile gas measuring device 3a can always be carried out in a short time and adapted to the local conditions and needs.

Figure 2:
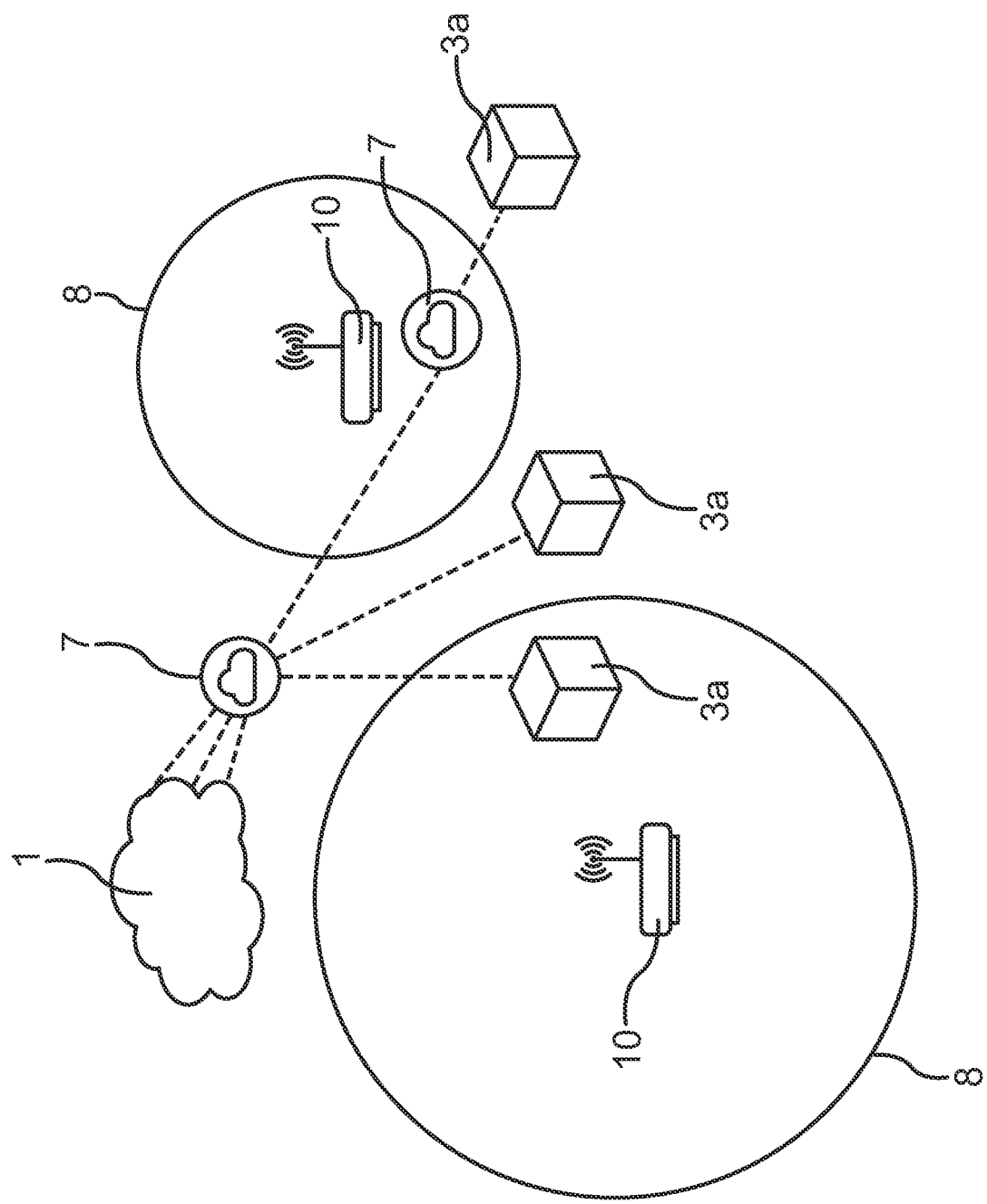
FIG. 2 is a schematic view showing different zones of a production site.

FIG. 2 shows in a schematic view a system according to the present invention for implementing a process for monitoring the concentration of gases and/or gas mixtures at a production site. The production site has been divided into different zones 8 as a function of the conditions and safety requirements prevailing there. The corresponding zones 8 are stored in the central data processing unit 1. Zone-specific parameters, which take into consideration, for example, the light and noise conditions prevailing in the assigned zone 8, the expectable contamination of the air with dust and/or vapor, gases or gas mixtures to be potentially expected to be present in the zone, a hazard potential, an accessibility, plants and plant parts present in the zone and/or tools, measuring devices and/or qualifications needed for work in the zone, are assigned to each of these zones 8.

Furthermore, location-specific information, i.e., information on the respective location of a gas measuring device, is transmitted for each mobile gas measuring device 3a, preferably with the generated measured data or other data, to the central data processing unit 1. The transmission of the location information may take place directly from a mobile gas measuring device 3a to an interface 5 of the central data processing unit 1 or else via an intermediate transceiver unit 9, e.g., a mobile phone. Gateways 7, which may be integrated, for example, into a stationary gas measuring device 3a or into a transmitter unit, and via which data are transmitted from a mobile gas measuring device 3a located within the range to the interface 5 of the central data processing unit 1 and are enriched with information on the respective location of the mobile gas measuring device 3a, are provided in some areas of the production site. As an alternative or in addition, mobile transceiver units 9, especially mobile phones, with gateways 7 are used in order to add information on the location at which the respective mobile gas measuring device 3a is located to the data transmitted from a mobile gas measuring device 3a.

Information on the location of a mobile gas measuring device 3a is thus always available in the central data processing unit 1, so that a zone 8 with the at least one zone-specific parameter valid for this zone 8 can be assigned to the corresponding location. Functionalities and/or device-specific settings or parameters of the mobile gas measuring device 3a are set, adapted and/or changed now corresponding to the conditions prevailing in the zone 8 and to the applicable safety requirements on the basis of the at least one zone-specific parameter. It is possible in this manner, for example, to carry out a selection of the type of alarm generation, a setting of a limit value or threshold value, a setting of the measurement to be carried out, a selection of the sensor to be used and/or a performance of any possible updates adapted to the zone 8, in which the mobile gas measuring device 3a happens to be located. Messages on a change of the zone 8 can likewise be outputted to the device user and transmitted to other people and/or to the control room of the production site.

According to the exemplary embodiment shown in FIG. 2, so-called implicit zones 8 are set. Mobile gas measuring devices 3a, gateways 7 or other mobile or stationary devices enrich the transmitted data in the implicit zones 8 with information in relation to the location of a mobile gas measuring device 3a, and the information on the location of the mobile gas measuring device 3a is provided by a localization module 10 according to the embodiment shown in FIG. 2. Such a localization module 10 is embodied by a hardware component, e.g., a Bluetooth module; it is positioned stationarily on site and it continuously transmits an identifier, which contains information on the location. An implicit zone 8 is thus formed around the localization module 10 within the transmission range, and generally different information can be added to the data finally transmitted by the mobile gas measuring device 3a.

According to a special embodiment, a mobile or stationary gateway 7 receives the location information from a localization module 10 arranged in a zone 8. The data transmitted via the gateway 7 are then enriched with this information. The range of the localization module 10 can hereby be extended by the range of the gateway 7. According to this embodiment, the information on the location is thus not present in the mobile gas measuring device 3a itself, but it is made available by the localization module and is transmitted by the mobile gas measuring device 3a together with the data generated by the mobile gas measuring device 3a to the closest gateway 7. The data, which are now enriched with the location information and are processed in this manner, can be transmitted from here to the interface 5 of the central data processing unit 1. It is not necessary according to this technical solution for the gateway 7 to receive the identifier itself, which is transmitted by the location module 10, because the mobile gas measuring device 3a enriches the transmitted data with the location information.

According to another embodiment, it is conceivable that a gateway 7 is used itself as a localization module 10. It is possible now especially in case of stationary gateways 7 to do without an additional hardware component and to assign the information on the respective zone 8 and hence on the location of a mobile gas measuring device 3a, which transmits data via the gateway 7 at least indirectly to the interface 5 of the central data processing unit 1, permanently to the gateway 7.

In addition to implicit zones, explicit zones are, furthermore, provided. Explicit zones are characterized compared to implicit zones by the fact that these are set in the monitored system via a defined set of location information. For example, a central coordinate is set here within the zone, e.g., by means of a GPS module, and the outer edges of the zone are set by a radius or boundary points as a polygon, likewise as a function of GPS coordinates. The coordinates are preferably stated in the GPS format, but it is also possible to use equivalent coordinate formats.

A plurality of zones 8, which may be implicit or explicit zones, are stored in this manner in the central data processing unit 1. Furthermore, a data transmission takes place either directly from a mobile gas measuring device 3a or via a gateway 7 to the interface 5 of the central data processing unit 1, which interface is intended for this purpose, wherein the transmitted data are enriched with information on the location of the mobile gas measuring device 3a. A comparison is then carried out in the central data processing unit 1 between the location of the respective mobile gas measuring device 3a and the existing zone information, so that each mobile gas measuring device 3a can finally be assigned to a zone 8. On the basis of the zone-specific parameters defined for each zone 8, the current functionality of the mobile gas measuring device 3a is then checked in order to be changed or adapted as needed in case of changing needs and conditions. If it is determined in the central data processing unit 1 that a mobile gas measuring device 3a is located in one of the zones 8 defined in the system, it is possible to note the location in the central data processing unit 1. Taking this determination into consideration, data, which are transmitted from this zone 8 to the central data processing unit 1, are not, for example, taken into consideration or are processed in a prioritized manner, especially in order to carry out a special action, e.g., the generation of a special alarm signal or an alarm analysis, and/or to perform a masking of certain data, especially personal data.

It is, furthermore, conceivable to notify mobile gas measuring devices 3a depending on the assigned zone 8 by the central data processing unit 1 that a change from one zone to another has taken place and hereby to notify the device user of the change from one zone to another and/or of a change of an operating mode having taken place.

Figure 3:
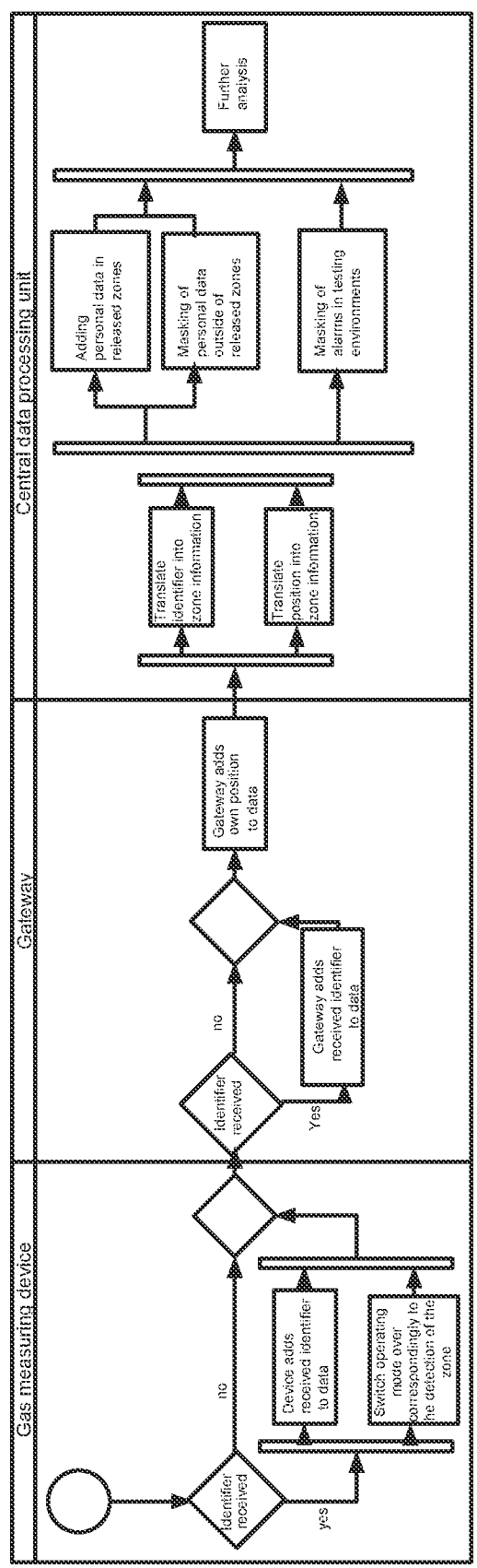
FIG. 3 is a flow chart showing a change in the operating mode in a mobile gas measuring device on the basis of the detection of a change from one zone into another.

It is thus possible to change over the operating mode as needed in an automated manner in the mobile gas measuring device and thus to adapt the functionality of the mobile gas measuring device to the conditions and to the safety requirements of the respective zone as needed. The procedure of changing over an operating mode, in which a mobile gas measuring device is operated, during a change from one zone to another is shown in FIG. 3 in a flow chart. It is possible, for example, in this connection that the mobile gas measuring device 3a is brought into a maintenance mode when a safe zone is reached, alarms are not outputted acoustically via the gas measuring device and/or that blocking functions provided in the devices, which functions are triggered by elapsed checking intervals, are not active any longer.

Further, it is possible to set at least one test zone. in which a mobile gas measuring device 3a is switched to a special testing mode, in which the device 3a changes automatically over into a testing and/or calibration mode. In addition, special functionalities, e.g., a configuration mode, are conceivable, so that the mobile gas measuring device 3a receives a software update or a firmware update in certain zones only.

As is shown by the above explanations, the present invention makes it possible by a division of a production site into specific zones 8 and by the assignment of zone-specific parameters for the respective mobile gas measuring devices 3a used to be operated as needed depending on their location in one of the specified zones 8 and on the conditions existing here and on the applicable safety requirements. A mobile gas measuring device 3a can be switched in this manner rapidly and reliably to the respective operating mode, so that the functionalities of the mobile gas measuring device 3a, which are needed in a zone 8, are achieved, without the device user himself having to take any action for this purpose. The safety for the user of mobile gas measuring devices 3a is markedly increased by means of such a system without essential interventions having to be made for this purpose in the hardware of the mobile gas measuring devices 3a.

While specific embodiments of the invention have been shown and described in detail to illustrate the application of the principles of the invention, it will be understood that the invention may be embodied otherwise without departing from such principles.

1 Data processing unit
  2 Data analysis unit
  3a Mobile gas measuring device
  3b Stationary gas measuring device
  4 Central memory
  5 Interface of the data processing unit
  6 Internal memory
  7 Gateway
  8 Zone
  9 Transceiver unit
  10 Localization module
  11 Control unit of the mobile gas measuring device

What is claimed is:

1. A process for changing a behavior of at least one mobile gas measuring device, the process comprising the steps of:
    generating data by the at least one mobile gas measuring device, which is located in the monitored area, based on a gas concentration measurement and transmitting the data to a central data processing unit;
    comparing the data generated based on the gas concentration measurement with at least one limit value and outputting an information signal based on an undershooting or overshooting of the limit value by the at least one mobile gas measuring device or by the central data processing unit or by both the at least one mobile gas measuring device and the central data processing unit;
    detecting a current position of the at least one mobile gas measuring device;
    dividing the monitored area into a plurality of zones and setting zone-specific parameters for each of the plurality of zones; and
    setting or changing or setting and changing an operating mode, which comprises a plurality of functions, to a changed-over operating mode, which comprises less than the plurality of functions, based on the current position of the gas measuring device and based on at least one of the zone-specific parameters.

2. The process in accordance with claim 1, wherein at least one functionality is set or changed or set and changed, wherein the at least one functionality comprises one or more of: a sensitivity; a limit value stored in the at least one mobile gas measuring device; an alarm output loudness; and a setting of a display unit of the at least one mobile gas measuring device.

3. The process in accordance with claim 1, wherein the at least one mobile gas measuring device outputs information upon the at least one mobile gas measuring device being moved from one zone into another zone.

4. The process in accordance with claim 1, wherein: the central data processing unit includes an interface; and a data transmission is started or ended between the at least one mobile gas measuring device and the interface of the central data processing unit based on the current position of the at least one mobile gas measuring device and based on at least one of the zone-specific parameters.

5. The process in accordance with claim 1, wherein a calibration procedure or test procedure is started or ended in the at least one mobile gas measuring device based on the current position of the at least one mobile gas measuring device and based on at least one of the zone-specific parameters.

6. The process in accordance with claim 1, wherein a firmware update or a software update or both a firmware update and a software update is started or ended based on the current position of the at least one mobile gas measuring device and based on at least one of the zone-specific parameters.

7. The process in accordance with claim 1, wherein a stationary localization module is arranged in at least one zone of the monitored area and the stationary localization module transmits an identification signal specific of the zone in which the stationary localization module is arranged.

8. The process in accordance with claim 7, wherein:
the identification signal is received by the at least one mobile gas measuring device or by a gateway, via which the at least one mobile gas measuring device transmits data to an interface of the central data processing unit; and
information on the position of the at least one mobile gas measuring device or on the zone in which the at least one mobile gas measuring device is located or both on the position of the at least one mobile gas measuring device and on the zone in which the at least one mobile gas measuring device is located is added to the data transmitted from the at least one mobile gas measuring device, directly or via the gateway, to the interface of the central data processing unit based on the received identification signal.

9. The process in accordance with claim 1, wherein a data transmission from the at least one mobile gas measuring device to an interface of the central data processing unit takes place via a gateway arranged stationarily in the monitored area; and the gateway adds information, on the position of the at least one mobile gas measuring device or on the zone in which the at least one mobile gas measuring device is located or both on the position of the at least one mobile gas measuring device and on the zone in which the at least one mobile gas measuring device is located, to the data transmitted by the at least one mobile gas measuring device.

10. The process in accordance with claim 1, wherein:
at least one stationary gas measuring device is arranged in the monitored area;
the stationary gas measuring device generates data based on a gas concentration measurement and transmits the data to an interface of the central data processing unit;
the data generated based on the gas concentration measurement are compared with at least one limit value; and
an information signal is outputted based on an undershooting or overshooting of the limit value by the at least one stationary gas measuring device or by the central data processing unit or by both the at least one stationary gas measuring device and by the central data processing unit.

11. The process in accordance with claim 10, wherein the information signal is transmitted to the at least one mobile gas measuring device.

12. The process in accordance with claim 10, wherein a localization module is arranged at the stationary gas measuring device and the localization module transmits an identification signal specific of the zone in which the stationary gas measuring device is located.

13. The process in accordance with claim 1, further comprising:
setting or changing or setting and changing a type of alarm generation of the at least one mobile gas measuring device based on the current position of the gas measuring device and based on the at least one of the zone-specific parameters, the one operating mode being one of a measuring mode, a testing mode, a configuration mode, a calibration mode and a maintenance mode, the another operating mode being another one of the measuring mode, the testing mode, the configuration mode, the calibration mode and the maintenance operating mode, wherein the zone-specific parameters are set based on one or more of: light and noise conditions prevailing in the assigned zone; and a contamination of the air with dust; and vapor, gas, and gas mixtures to be expected to be potentially present in the zone; a hazard potential; an accessibility; plants and plant parts present in the zone; and tools needed for work in the zone.

14. The process in accordance with claim 1, wherein the at least one mobile gas measuring device is configured to be in a maintenance mode when the at least one mobile gas measuring device is in a safe zone.

15. The process in accordance with claim 14, wherein the at least one mobile gas measuring device is configured to not provide an alarm as output when the at least one mobile gas measuring device is in the safe zone.

16. A process for changing a behavior of at least one mobile gas measuring device, the process comprising the steps of:
generating data by the at least one mobile gas measuring device, which is located in the monitored area, based on a gas concentration measurement and transmitting the data to a central data processing unit;
comparing the data generated based on the gas concentration measurement with at least one limit value and outputting an information signal based on an undershooting or overshooting of the limit value by the at least one mobile gas measuring device or by the central data processing unit or by both the at least one mobile gas measuring device and the central data processing unit;

detecting a current position of the at least one mobile gas measuring device;

dividing the monitored area into a plurality of zones and setting zone-specific parameters for each of the plurality of zones; and setting or changing or setting and changing an operating mode of the at least one mobile gas measuring device, which comprises a plurality of functions, to a changed-over operating mode of the at least one mobile gas measuring device, which comprises less than the plurality of functions, based on the current position of the gas measuring device and based on at least one of the zone-specific parameters.

17. The process in accordance with claim 16, wherein the operating mode is set and/or changed to adapt a functionality of the mobile gas measuring device to conditions and to safety requirements of a respective one of the plurality of zones, the operating mode being one of a measuring mode, a testing mode, a configuration mode, a calibration mode and a maintenance mode, the changed-over operating mode being another one of the measuring mode, the testing mode, the configuration mode, the calibration mode and the maintenance mode.

18. The process in accordance with claim 17, wherein the mobile gas measuring device is brought into the maintenance mode when a safe zone is reached, alarms are not outputted acoustically via the mobile gas measuring device and/or blocking functions provided in the mobile gas measuring device, which functions are triggered by elapsed checking intervals, are not active.

* * * * *